United States Patent [19]
McNally et al.

[11] Patent Number: 5,874,112
[45] Date of Patent: *Feb. 23, 1999

[54] TRANSLUCENT ANTACID SUSPENSION

[75] Inventors: Gerard P. McNally, Strafford; John J. Dubek, Philadelphia, both of Pa.

[73] Assignee: McNeil PPC-Inc., New Brunswick, N.J.

[*] Notice: This patent issued on a continued prosecution application filed under 37 CFR 1.53(d), and is subject to the twenty year patent term provisions of 35 U.S.C. 154(a)(2).

[21] Appl. No.: 828,622

[22] Filed: Mar. 31, 1997

[51] Int. Cl.$^6$ .................................................. A61K 33/08
[52] U.S. Cl. ............................................................ 424/690
[58] Field of Search ............................................. 424/690

[56] References Cited

U.S. PATENT DOCUMENTS

| | | | |
|---|---|---|---|
| 1,949,266 | 2/1934 | Bird | 167/55 |
| 2,137,638 | 11/1938 | Sondern et al. | 23/143 |
| 2,783,179 | 2/1957 | Grote . | |
| 2,999,790 | 9/1961 | Alford | 167/55 |
| 3,395,221 | 7/1968 | Snyder et al. | 424/157 |
| 3,735,007 | 5/1973 | Lapidus . | |
| 3,843,778 | 10/1974 | Diamond et al. | 424/38 |
| 3,892,851 | 7/1975 | Hinkel | 424/157 |
| 4,533,543 | 8/1985 | Morris et al. | 424/38 |

FOREIGN PATENT DOCUMENTS 2512344  3/1983  France .
WO 94/13304  6/1994  WIPO .

OTHER PUBLICATIONS

Handbook of Sweeteners, Edit. S. Marie & J.R. Piggot, Blackie & Son, Ltd. "Sugar Alcohols", pp. 72–103 (1991).

Encyclopedia of Pharmaceutical Technology, J. Swarbrick, J. C. Boylan, (Eds.), vol. 3, "Colloids and Colloid Drug Delivery Systems", pp. 31–63 (1990).

Shah et al., Journal of Pharmaceutical Sciences, 70–1101–1104, (1981).

Nail et al., Journal of Pharmaceutical Sciences, 65:1188–1191 (1976).

Serna et al., Journal of Pharmaceutical Sciences, 67:1179–1181 (1978).

Nail et al., Journal of Pharmaceutical Sciences, 65:1195–1198 (1976).

*Primary Examiner*—Raymond Henley, III
*Attorney, Agent, or Firm*—Connolly and Hutz

[57] ABSTRACT

An essentially translucent antacid composition is formed by an aqueous colloidal aluminum hydroxide gel wherein the average particle size of the aluminum hydroxide is less than about 0.5 microns, preferably less than about 0.1 microns, and more preferably less than about 0.01 microns. The suspension is further preferably mixed with a polyol, such as sorbitol or maltitol, to enhance the translucency. The weight ratio of polyol to aluminum hydroxide gel (USP) ranges from about 0.5:1.0 to about 4.0:1.0.

20 Claims, No Drawings

TRANSLUCENT ANTACID SUSPENSION

FIELD OF THE INVENTION

The invention pertains to antacid compositions and methods for their preparation. More particularly, the invention relates to essentially translucent antacid compositions comprising aluminum hydroxide gel having a particle size of less than 0.5 microns, preferably less than 0.1 microns, wherein the suspension also preferably contains polyol.

BACKGROUND AND PRIOR ART

Antacid suspensions are standard medications for the treatment of heartburn and other gastrointestinal disorders. Antacids neutralize the gastric acids created in the stomach. It is desirable that an antacid feature a high acid neutralization capacity and a rapid rate of gastric acid neutralization.

Antacids are available in the form of liquid suspension or solid dosage forms. A major benefit of the liquid antacid form is that it acts more quickly than a solid to neutralize gastric acid. A disadvantage associated with antacids in general (both liquid and solid forms) is an undesirable chalky taste.

It is known in the art that conventional milling or homogenizing of antacid suspensions alleviates the chalkiness to some degree but not entirely. For example, U.S. Pat. No. 4,533,543 (Morris et al.) describes improving the texture of solid antacid formulations by maintaining a small particle size, e.g. less than 500 millimicrons, and coating the particles with a mixture comprised of a fatty material or oil. U.S. Pat. No. 3,843,778 (Diamond) also discloses coating solid antacid particles, ranging in size from 0.05 to 300 microns, with an oil to create an improved texture.

French Patent 2,512,344 discloses an antacid suspension of aluminum hydroxide or magnesium hydroxide added in powder form to water, in which the powder is then mechanically fragmented and dispersed until the mean particle size is 5-10 microns. International Application PCT/US93/11720 discloses an antacid composition comprising particles consisting essentially of an aluminum-based neutralization agent, e.g. aluminum hydroxide, wherein the particles are in discrete crystalline form. The particles have an average particle size of less than about 3 microns. Coarse particles of aluminum-based neutralizing agent are dispersed in a liquid media in which it is insoluble and subsequently ground to achieve the desired particle size. The antacid composition may contain from 5 to 80% by weight of said particles.

U.S. Pat. No. 3,892,851 (Hinkel) describes a clear antacid solution comprising water and an effective amount of polymeric meglumine-hexitol-aluminum hydroxide complex. In some formulations the composition must stand for two weeks before it becomes clear. Hinkel teaches that polymeric meglumine must be present for a clear antacid solution to be formed.

It is known in the art to use linear polyols, such as mannitol and sorbitol, with aluminum hydroxide gels to inhibit the polymerization reaction that occurs on aging. Shah et al., 70 J. Pharm. Sci. 1101–1104 (Oct. 1981), teaches that polyols also have a negative effect on the action of aluminum hydroxide gels by reducing the rate of acid neutralization, which occurs when the aluminum hydroxide concentration is correspondingly reduced. Shah discloses that by carefully selecting a specific polyol and corresponding concentration, gel stabilization can be optimized.

There is a need in the art to provide a liquid antacid composition of aluminum hydroxide gel that is non-chalky and translucent in appearance. Translucency appeals to the patient or user because it connotes purity and good mouth feel, as opposed to the chalky, granular taste normally associated with liquid antacids. There is also a need for simple and economical preparation of such formulations, which do not require long periods of time for the solution to clear.

SUMMARY OF THE INVENTION

The invention comprises an essentially translucent liquid antacid composition comprising an aqueous colloidal aluminum hydroxide gel, wherein essentially 100% of the aluminum hydroxide particles are less than about 0.5 microns, and preferably less than about 0.1 microns. The gel is preferably combined with one or more polyols to further enhance the translucency. Suitable polyols include sorbitol or maltitol, the polyol being provided preferably in a weight ratio of about 0.5 parts polyol to about 1 part colloidal aluminum hydroxide gel, to about 4 parts polyol to 1 part colloidal aluminum hydroxide gel.

The resulting solution is essentially translucent. By essentially translucent is meant translucent to the naked eye. In optical measurements, the composition would typically measure less than about 2000 NTU (Nephelometric Turbidimetric Units), preferably less than about 1500 NTU, and more preferably less than about 1000 NTU. The concentration of the effective ingredient can vary widely, and thereby vary the measured NTU, so the stated NTU values are not meant to be limiting in any way. Most importantly, the invention herein achieves translucency while maintaining a high ANC (acid neutralizing capacity).

The composition of the invention provides fast-acting antacid relief, yet has good mouth feel characteristics and desirable appearance. The antacid suspension retains substantial efficacy and translucency over a standard shelf life as long as one to two years. Furthermore, the antacid formulation is slow settling and exhibits thixotropic properties.

DESCRIPTION OF THE PREFERRED EMBODIMENTS

Aluminum hydroxide is known as an effective antacid active ingredient. Aluminum hydroxide is prepared by adding an alkali metal carbonate or bicarbonate to a solution of aluminum chloride or aluminum nitrate to produce an aluminum hydroxide gel of good efficacy in neutralizing gastric acid. For example, U.S. Pat. Nos. 4,576,819 and 4,105,579 teach preparation of aluminum hydroxide gels, and these disclosures are incorporated by reference.

The precipitation of aluminum hydroxide gel through the hydrolysis of an aluminum salt is complex. The precipitation method and subsequent treatment have a great effect on the properties of the product. Applicants produce an essentially translucent gel by stopping the precipitation reaction at a low pH. The carbonate or bicarbonate addition should be stopped when a pH of no higher than about 6.5 is reached. Though this produces a strong gel which can be difficult to wash, it has the significant advantage of being essentially translucent.

In the colloidal aluminum hydroxide gel employed in compositions of the present invention, all of the particles are less than about 0.5 microns in size, preferably less than about 0.1 microns, and more preferably less than about 0.01 microns. The particle size may be determined by diluting a sample of the suspension with 49% ammonium hydroxide, 49% water and 2% triton, and allowing it to air dry.

Scanning electron micrographs of the resulting samples are then analyzed to determine particle size. When the particle size is less than about one micron, the aluminum hydroxide is considered colloidal in the gel. The gel suspension produced by the method of the invention herein has an essentially translucent appearance and preferably an $Al(OH)_3$ content (equivalent to dried gel, USP 23) of 4.0 to 10.0%, preferably 7.0 to 9.0%.

In accordance with the present invention, the translucency of the aqueous aluminum hydroxide compositions having the specified particle size range is greatly enhanced by adding a polyol. By polyol is meant a non-toxic, pharmaceutically acceptable polyhydric alcohol. The polyol component of the invention comprises a polyol that when added to the aluminum hydroxide gel increases translucency. The preferred polyols are sugar alcohols. The polyol is preferably in the form of a solid powder or an aqueous solution concentrated to 50–80% polyol. The most preferred polyols include hydrogenated monosaccharides such as sorbitol and hydrogenated disaccharides such as maltitol. The weight ratio of polyol to aluminum hydroxide gel is between about 0.5:1.0 and about 4.0:1.0. The weight ratio of polyol to aluminum hydroxide gel to water is typically about 1:1:2.

Other components of the liquid antacid suspension are well-known formulation aids typically found in pharmaceutical suspensions, such as suspending agents, antigelling additives, surface modifiers, preservatives, sweeteners, flavorants, waxes, colorants and diluents. Suitable additives are, for example, hydroxyethyl cellulose, hydroxypropyl methyl cellulose, sugars, sugar alcohols, saccharin, salts, parabens, such as butyl and methyl parabens, and ethylenediamine tetra-acetic acid. Other active ingredients may be present, such as antifoaming agents like simethicone, histomine $H_2$-receptor antagonists like cimetidine, ranitidine, nizatidine or famotidine, and proton-pump inhibitors such as omeprazole and lansoprazole.

A preferred finished formulation for the liquid antacid composition of the invention herein contains the following (wherein the relative amounts of ingredients are expressed as weight percentages based on the total weight of the finished formulation): about 10% to about 50% of an aqueous colloidal aluminum hydroxide gel as disclosed herein, about 5% to about 50% polyol, 0% to about 85% water, about 0.1% to about 1.0% suspending agent, about 0.01% to about 0.05% propyl paraben, about 0.01% to about 0.05% butyl paraben and about 0.01% to about 1.5% flavorants. A preferred suspending agent is hydroxyethyl cellulose.

By way of explanation, it is understood that those skilled in the art need only understand the nature of the recipe for the starting materials in order to make the composition of the invention herein. It is well understood in this particular art that one can describe the final product by referring back to the precursor or starting materials, since such a description is sufficient for the reproducibility of the product.

In the method of the present invention, the composition of the invention is preferably prepared by the following procedure. The polyol is first dissolved in water. Optionally, a suspending agent, such as hydroxyethyl cellulose, may be added to the polyol/water mixture and mixed until the polyol and optional surface active agent are completely dissolved. Aluminum hydroxide gel is added to the aqueous polyol mixture with high speed agitation. The actual ratio can be adjusted to achieve the desired concentration of aluminum hydroxide and the desired degree of translucency. When the aluminum hydroxide gel has been dispersed in the polyol solution, other optional formulation aids may be added. The suspension is then homogenized and pasteurized.

The invention may be further illustrated by the following examples, which are provided to illustrate, but not limit the scope of the invention

EXAMPLE 1

(sorbitol)

(A) Preparation of colloidal aluminum hydroxide gel suspension

An aluminum chloride solution was prepared by slowly dissolving 300 grams of $AlCl_3$ hexahydrate in 700 grams of deionized water. A sodium carbonate solution was prepared by dissolving 370 grams sodium carbonate in 630 grams of deionized water. The sodium carbonate solution was slowly added to the aluminum chloride solution until a pH of 6.0 was achieved. A gel was formed which was stirred for one hour. The colloidal aluminum hydroxide gel was then filtered using a Buchner funnel and washed with deionized water to remove soluble impurities. The washed gel had an aluminum hydroxide (equivalent to dried gel, USP 23) content of approximately 8.0%.

(B) Formulation of Antacid Composition

The colloidal aluminum hydroxide gel prepared in step (A) was used to produce a liquid antacid formulation. An aqueous sorbitol solution was prepared by mixing 2838 grams of deionized water and 1800 grams of a 70% sorbitol solution in a 15 liter vessel equipped with an IKA mixer. With the agitator set at high speed, 30 grams of hydroxyethyl cellulose was added to the aqueous sorbitol mixture. The hydroxyethyl cellulose used was NATROSOL 250 Pharm, available from Hercules, which has a viscosity at 2% concentration of 4,500–6,500 cps.

Once the hydroxyethyl cellulose was dissolved, 2500 grams of colloidal aluminum hydroxide gel produced in step (A) was added to the mixture vessel also with high speed agitation. Once the gel was completely dispersed, the following were added in sequence: 2 grams sodium ethylene diamine tetra-acetic acid, 400 grams maltitol powder, 45 grams of PROSWEET G (a flavor additive/enhancer sold by Virginia Dare), 2 grams butylparaben, 3 grams propylparaben, 3.5 grams mint flavor, and lastly 2400 grams of deionized water. The mixture was homogenized and pasteurized and the resulting suspension was substantially entirely translucent in appearance to the naked eye.

EXAMPLES 2–5 (maltitol)

The aluminum hydroxide gel from Example 1 (A) was mixed with water and stirred until it was free of lumps. Maltitol was then added in the following weight proportions with stirring to yield suspensions with the turbidity indicated in Table I:

TABLE I

| Example | % Maltitol | % Water | % $Al(OH)_3$gel | Turbidity (NTU) |
|---|---|---|---|---|
| 2 | 0 | 75 | 25 | 1750 |
| 3 | 15 | 60 | 25 | 1367 |
| 4 | 25 | 50 | 25 | 1151 |
| 5 | 35 | 40 | 25 | 979 |

The level of translucency is measured by comparing NTU values (nephelometric turbidimetric units) of turbidity. As can be seen from Table I, at equivalent levels of aluminum hydroxide, the turbidity of the aluminum hydroxide gel is increasingly reduced by added malitol, and is reduced by almost 50% with the addition of 35% by weight of maltitol.

EXAMPLES C1–C3 and 6–9
(maltitol)

Table II shows turbidity measurements for examples 6 and 8 prepared according to the invention, examples 7 and 9 additionally containing 50% by weight maltitol solution, and also turbidity measurements for comparative examples C1–C3.

TABLE II

| Example | Formula | Turbidity, NTU's | ANC mEq./per 15 ml. |
|---|---|---|---|
| C1 | D.I. water | 0.14 | — |
| C2 | Aluminum hydroxide gel-commercial | >2000 | 9.00 |
| C3 | Aluminum hydroxide gel-commercial | >2000 | 3.00 |
| 6 | 30% CAG in water | 714 | 10.80 |
| 7 | 30% CAG in Maltitol water mixture | 309 | 10.80 |
| 8 | 20% CAG in water | 395 | 7.20 |
| 9 | 20% CAG in Maltitol water mixture | 186 | 7.20 |

CAG = Colloidal Aluminum Hydroxide Gel
NTU = Nephelometric Turbidimetric Units measured using HACH Turbidimeters
ANC = Acid Neutralizing Capacity As Table II shows, the turbidity measured in NTU's of water is less than 1, whereas the turbidity of commercially available aluminum hydroxide gel is greater than 2000. Comparative Examples C1 and C2 contain commercially available aluminum hydroxide gel. To compare turbidity at equivalent ANC values, the commercial gel was diluted with water to achieve the stated ANC values.

A 30% colloidal aluminum hydroxide gel in water at an ANC activity of 10.80 mEq/per 15 ml (Example 6) has a turbidity value of 714 NTU. Example 7, also prepared in accordance with the invention, shows the surprising result that when a 30% colloidal aluminum hydroxide gel is suspended in a maltitol water mixture, the turbidity is reduced by more than 50%.

As shown in Examples 8 and 9, a similar result is achieved with a 20% colloidal aluminum hydroxide gel in a maltitol water mixture. Example 9 shows that turbidity is reduced by more than 50% as compared to Example 8, from 395 to 186 NTU's.

From these examples, it will be appreciated that the compositions of the invention allow for high acid neutralization levels of aluminum hydroxide while providing a translucent, liquid preparation. Table II also shows that the activity of the colloidal aluminum hydroxide gel is maintained with the addition of polyol, as measured soon after preparation of the antacid suspension.

Other embodiments of the invention will be apparent to those skilled in the art from consideration of the specification and practice of the invention disclosed herein.

What is claimed is:

1. An essentially translucent, liquid antacid composition comprising an aqueous colloidal aluminum hydroxide gel, wherein the aluminum hydroxide particles are less than about 0.5 microns in size.

2. The antacid composition of claim 1 wherein the aluminum hydroxide gel has an $Al(OH)_3$ content (equivalent to dried gel, USP 23) of from about 4.0% to about 10% by weight.

3. The antacid composition of claim 1 wherein the aluminum hydroxide gel has an $Al(OH)_3$ content (equivalent to dried gel, USP 23) of from about 7.0% to about 9% by weight.

4. The antacid composition of claim 1 wherein the particle size of the aluminum hydroxide gel is less than about 0.1 microns.

5. The antacid composition of claim 1 wherein the particle size of the $Al(OH)_3$ is less than about 0.01 microns.

6. The antacid composition of claim 1 wherein the composition additionally comprises a polyol to further enhance the translucency.

7. The antacid composition of claim 6 wherein the weight ratio of polyol to colloidal $Al(OH)_3$ gel is at least about 0.5.

8. The antacid composition of claim 7 wherein the polyol is a hydrogenated monosaccharide, hydrogenated disaccharide, or a mixture thereof.

9. The antacid composition of claim 8 wherein the polyol is sorbitol, malitol or a mixture thereof.

10. The antacid composition of claim 9 wherein the polyol is sorbitol.

11. The antacid composition of claim 9 wherein the polyol is malitol.

12. The antacid composition of claim 1 wherein the composition has a turbidity of less than 2000 NTU.

13. The antacid composition of claim 1 wherein the composition has a turbidity of less than 1500 NTU.

14. The antacid composition of claim 1 wherein the composition has a turbidity of less than 1000 NTU.

15. The antacid composition of claim 7, wherein the weight ratio of polyol to colloidal aluminum hydroxide gel ranges from about 0.5:1 to about 4:1.

16. The antacid composition of claim 11, wherein the weight ratio of maltitol to aluminum hydroxide gel is $\geq 1.0$.

17. The antacid composition of claim 6 comprising the following additional components expressed as weight percentages based on the total weight of the composition: up to about 85% water, about 0.1% to about 1.0% suspending agent, about 0.01% to about 0.05% propyl paraben, about 0.01% to about 0.05% butyl paraben, and about 0.1% to about 1.5% flavorant, wherein the polyol comprises about 5% to about 50% by weight, based on the total weight of the composition, and the aqueous colloidal aluminum hydroxide gel comprises about 10% to about 50% by weight based on the total weight of the composition.

18. A method for making an essentially translucent, liquid antacid composition with non-chalky consistency comprising:

(a) providing a aqueous colloidal aluminum hydroxide gel wherein essentially all of the aluminum hydroxide particles are less than about 0.5 microns in size; and (b) mixing the aluminum hydroxide gel with polyol in a weight ratio of polyol:gel of between 0.5:1.0 and 4.0:1.0 to provide a stable, translucent suspension.

19. The method of claim 18, wherein the polyol is sorbitol or maltitol.

20. An antacid composition produced by the method of claim 18.

* * * * *